United States Patent [19]

McGowan et al.

[11] Patent Number: 5,028,790
[45] Date of Patent: Jul. 2, 1991

[54] APPARATUS FOR FULL-SYSTEM ZERO CHECK AND WINDOW SOILING MEASUREMENT AND CORRECTION FOR TRANSMISSOMETERS

[75] Inventors: Gerald F. McGowan, Parker; Ronald L. Ketchum, Littleton, both of Colo.

[73] Assignee: Lear Siegler Measurement Controls Corporation, Englewood, Colo.

[21] Appl. No.: 520,074

[22] Filed: May 7, 1990

[51] Int. Cl.$^5$ .................................... G01N 15/06
[52] U.S. Cl. ............................... 250/573; 356/438
[58] Field of Search ............... 250/573, 574; 356/436, 356/437, 438, 439, 342

[56] References Cited

U.S. PATENT DOCUMENTS 3,860,818  1/1975  Stadler et al. ..................... 250/573
4,896,047  1/1990  Weaver et al. ..................... 250/573

OTHER PUBLICATIONS

Lear Siegler Measurement Controls Corporation Brochure Entitled, "Dynatron 1100M"; dated 10/89.

Primary Examiner—David C. Nelms
Assistant Examiner—K. Shami
Attorney, Agent, or Firm—Fields, Lewis, Pittenger & Rost

[57] ABSTRACT

The present invention relates to an apparatus which can be inserted between the stack and a transceiver of a transmissometer to provide zero and span measurements using the primary light source from the transceiver. The apparatus includes a calibration device mounted between the transceiver and one side of the stack and within the path of the light beam. A zero reflector is mounted within the calibration device for movement back and forth between an inactive position and an active position within the path of the light beam to reflect the same amount of light back into the transceiver as the retro-reflector would across the stack when the stack is clear of smoke. In addition, means is connected to the zero reflector for accomplishing this movement. A span filter is also provided within the calibration device which is movable between an active position in the light beam path to provide an upscale reference calibration check. The invention further contemplates a method of using the apparatus to establish zero and upscale references during initial set-up, followed by periodic establishment of new values indicative of soiling of the transceiver windows.

10 Claims, 3 Drawing Sheets

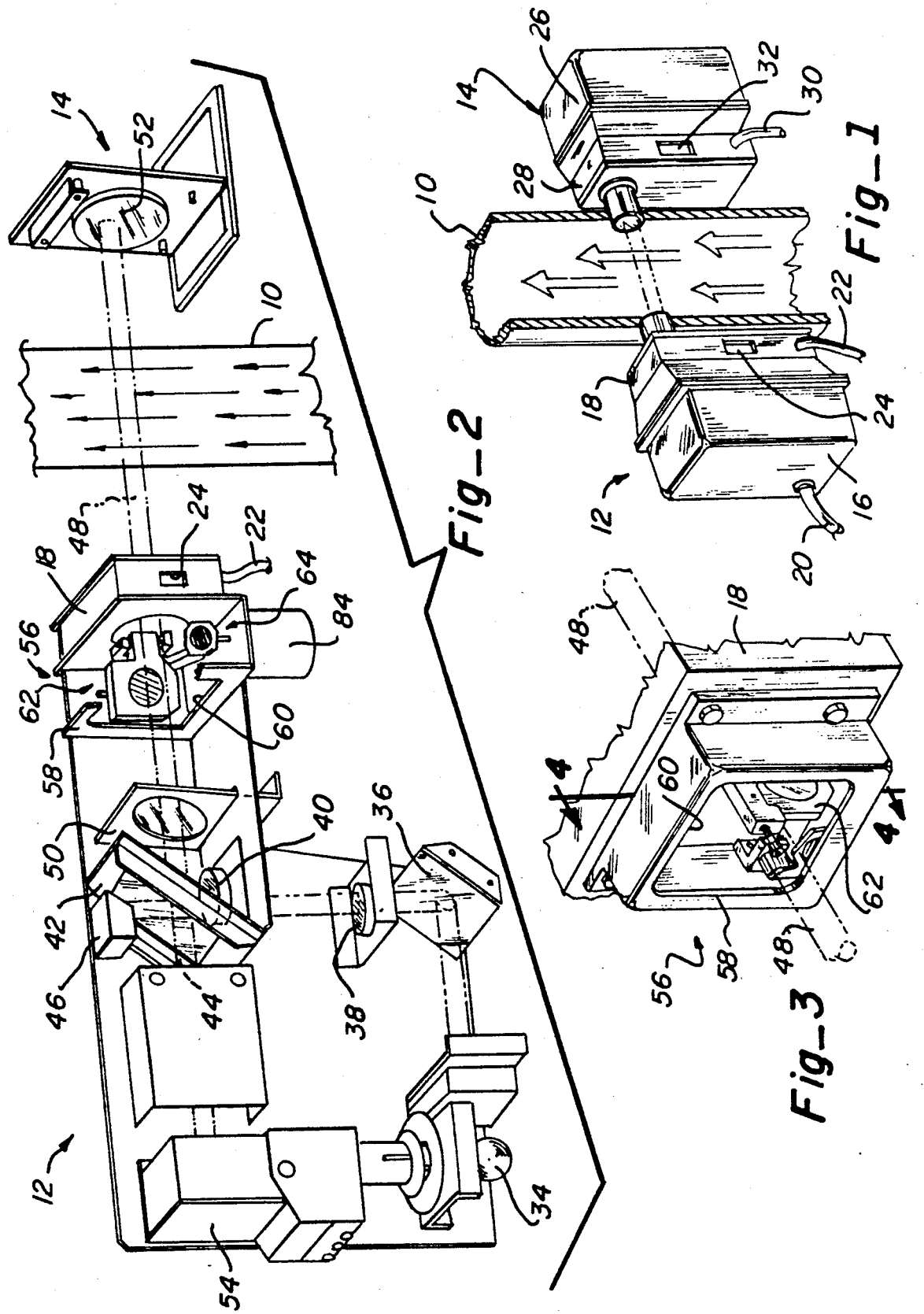

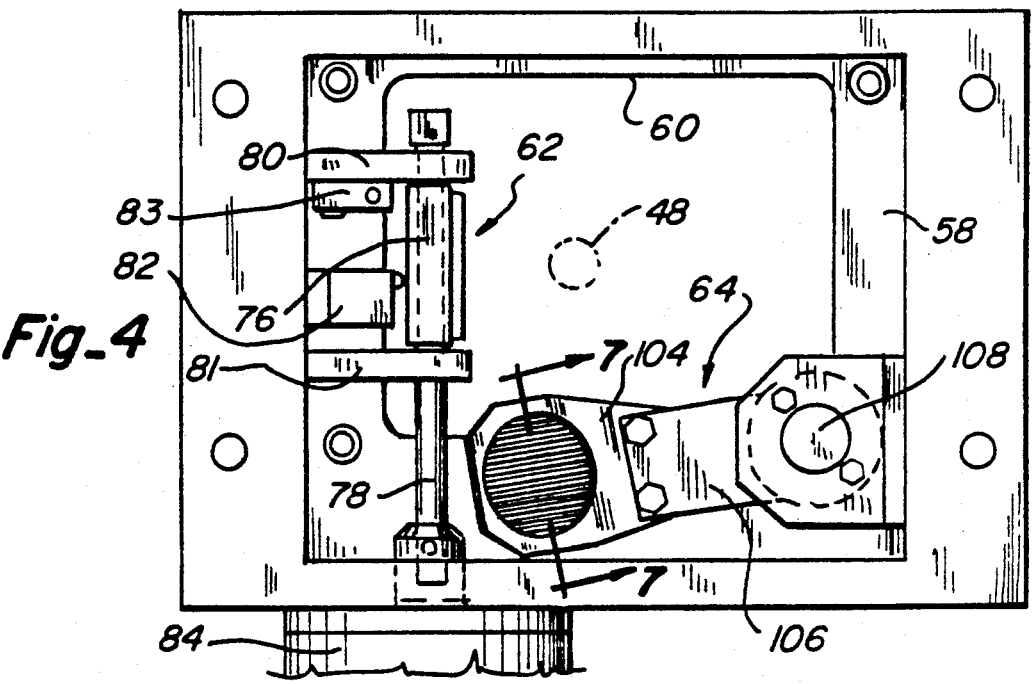
Fig_4
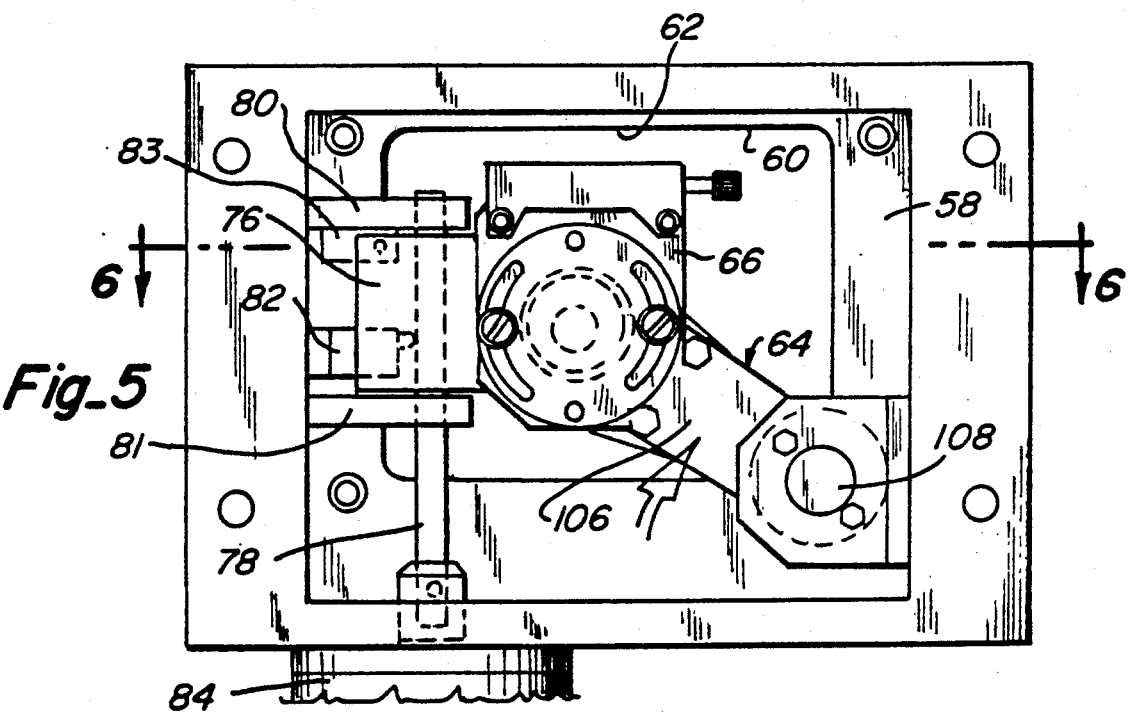
Fig_5
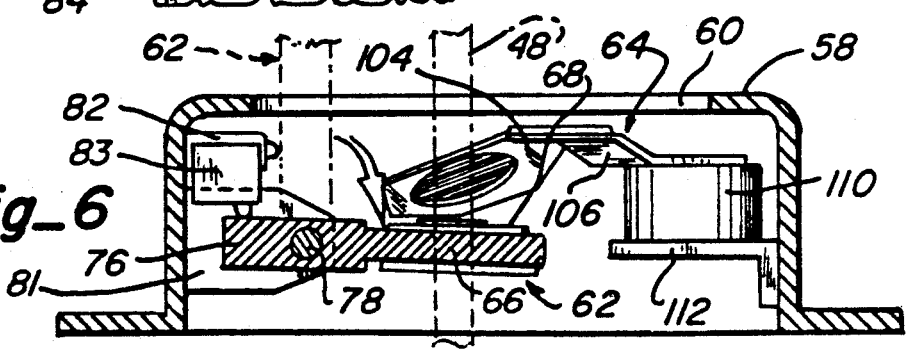
Fig_6

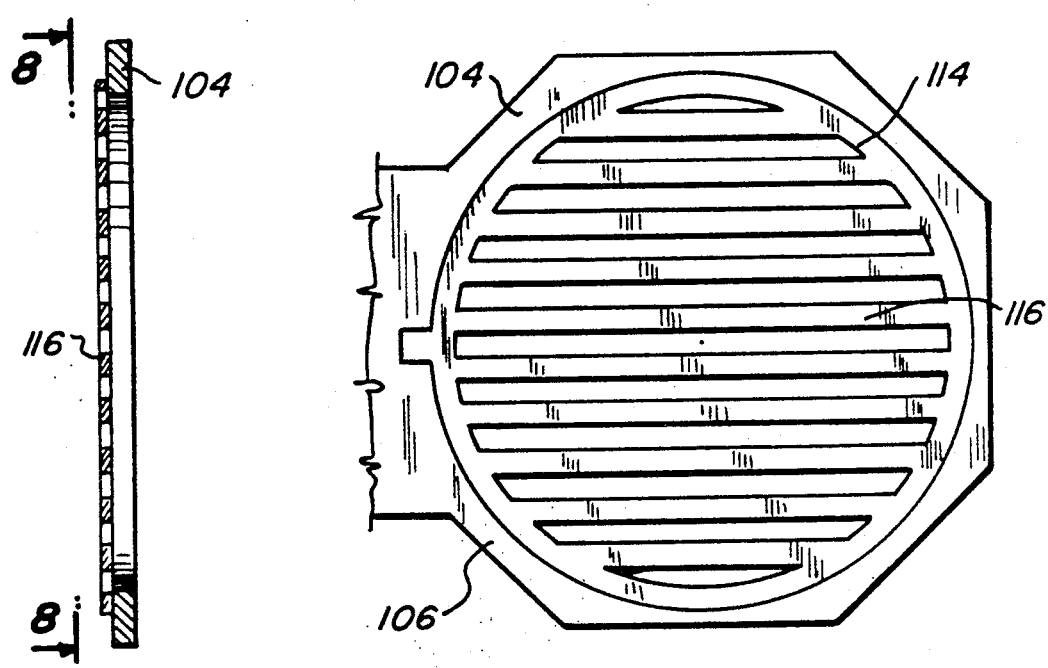
Fig._7  Fig._8
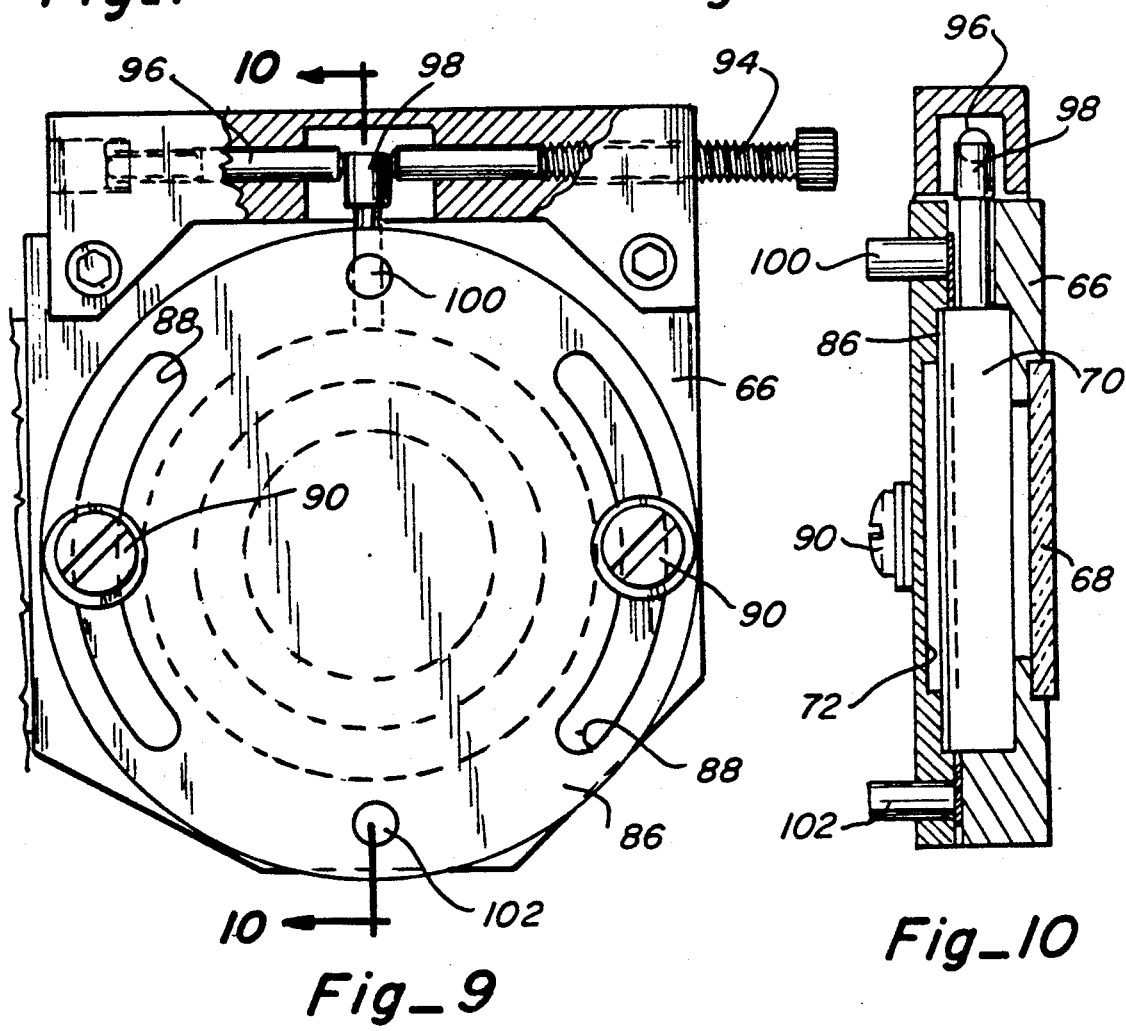
Fig._9  Fig._10

APPARATUS FOR FULL-SYSTEM ZERO CHECK AND WINDOW SOILING MEASUREMENT AND CORRECTION FOR TRANSMISSOMETERS

TECHNICAL FIELD

This invention relates to a zero check and window soiling measurement and correction device for transmissometers and more particularly for one in which the primary light source of the transmissometer is used for making the measurements.

BACKGROUND ART

A well-known and effective transmissometer is the Dynatron 1100M, a product of Lear Siegler Measurement Controls Corporation of Englewood, Colorado. It is a dual beam transmissometer which measures light transmittance through smoke and dust. It consists of two units: an optical transceiver mounted on one side of a stack or duct and a passive reflector mounted on the opposite side. Both the transceiver and the reflector are sealed to minimize condensation or deposits of dirt on optical surfaces.

The transceiver houses a light source, photodetector and glass fiber optics. A multiple lens condenser system assures uniform light radiation through the transceiver window for high accuracy. For calibration purposes, a multi-lamp calibration system is used wherein a first lamp is used to set the zero calibration and a second lamp for the span calibration. Periodically, the instrument is recalibrated to compensate for soiling of the window during use. Thus, the Dynatron 1100M uses three light sources. One lamp for the primary measurement, another for zero calibration and a third for span calibration. Both a reference and measurement detector are used to establish the appropriate measurements and short fiber optic cables are used to direct light from the applicable source of light to the detector. It can be seen that as the three lamps age, the amount of light output from each will decrease at different rates thereby affecting the accuracy of the readings obtained.

DISCLOSURE OF THE INVENTION

The present invention relates to an apparatus which can be inserted between the stack and the Dynatron 1100M transmissometer to provide zero and span measurements using the primary light source from a transceiver in the transmissometer. The apparatus includes a calibration device mounted between the transmissometer and one side of the stack and within the path of the light beam. A zero reflector is mounted within the calibration device for movement back and forth between an inactive position and an active position within the path of the light beam to reflect the same amount of light back into the transceiver as the retro-reflector would across the stack when the stack is clear of smoke. In addition, means is connected to the zero reflector for accomplishing this movement.

The apparatus can further include a filter mounted within the calibration device for movement from an inactive position to an active position within the path of the light beam and back again so that it is superimposed on the zero reflector to provide an upscale reference calibration check. In addition, means is connected to the filter for moving it between an inactive position and an active position. The zero reflector moving means can include a motor and the filter moving means can include a solenoid. The zero reflector and the filter are pivoted about different axes. The zero reflector can include an iris and have means for adjusting the iris for initial zero calibration.

It can be seen that the invention contemplates a method of projecting a light beam from the light source toward the retro-reflector, moving a zero reflector into the light beam on one side of the smoke stack, recording and storing a zero value indicative of a clear smoke stack, moving a filter into the light beam adjacent the zero reflector to cause the reflected light sensed by the transceiver to provide an upscale reference value and recording and storing the upscale reference value.

The invention contemplates the further method steps of moving the zero reflector and the filter to an inactive position out of the light beam path so that the light beam is projected across the stack and reflected back by the retro-reflector to the transceiver, recording the amount of light sensed by the transceiver over a predefined period of time, comparing the amount of light sensed by the transceiver over the predetermined period of time with the previously recorded zero value and upscale reference value to determine the opacity of smoke passing through the stack during the predetermined time period. The method further includes the steps of moving the zero reflector back into the light path at the end of the predetermined period of time, recording a zero offset value indicative of dirt accumulation on the window during the predetermined period, moving the filter back into the light path, recording a new upscale reference value, and repeating the earlier steps.

Thus, it can be seen that a novel but inexpensive apparatus has been provided wherein the main light source can be used for calibration purposes, as well as for use in measuring smoke density.

Additional advantages of this invention will become apparent from the description which follows, taken in conjunction with the accompanying drawings.

BRIEF DESCRIPTION OF THE DRAWINGS

FIG. 1 is a perspective view of a transmissometer positioned to measure opacity of smoke passing through a smoke stack;

FIG. 2 is a highly diagrammatic, partially exploded view of a transmissometer including the calibration apparatus of this invention;

FIG. 3 is a perspective view of the calibration apparatus of this invention;

FIG. 4 is an enlarged vertical section, taken along line 4—4 of FIG. 3, showing the calibration device with the zero reflector and filter in their inoperative position;

FIG. 5 is a view similar to FIG. 4, but showing both the zero reflector and the filter in operative position;

FIG. 6 is a horizontal section, taken along line 6—6 of FIG. 5, showing further details of the zero reflector and filter;

FIG. 7 is a generally vertical section, taken along line 7—7 of FIG. 4, showing details of the cross-section of the filter;

FIG. 8 is a fragmentary plan view, taken along line 8—8 of FIG. 7 of the filter;

FIG. 9 is an enlarged plan view of the zero reflector of this invention showing the adjustment means for the iris; and FIG. 10 is a vertical section, taken along line 10—10 of FIG. 9, showing further details of the zero reflector.

BEST MODE FOR CARRYING OUT THE INVENTION

As best seen in FIG. 1, a transmissometer is attached to stack 10 and has a transceiver 12 mounted on one side of the stack and a passive reflector 14 mounted on the other side. As will be more fully explained below, a light beam is transmitted by the transceiver 12 across the stack to a mirror mounted within passive reflector 14 which reflects the light back across the stack so that the light will be attenuated in accordance with the amount of particulate matter in the effluent discharged through the stack. The transceiver 12 includes a weather cover 16 connected to an air purge chamber 18 positioned between the cover and the stack. An electrical connector 20 is provided which extends through cover 16 to provide the electrical circuitry for the transceiver. An air hose 22 is connected to air purge chamber 18 for supplying air under pressure to keep the particulate material in the stack from entering the transceiver. This air can be exhausted through a port 24. Similarly, passive reflector 14 includes a weather cover 26. An air purge chamber 28 is positioned between cover 26 and stack 10 and is provided with an air pressure hose 30 through which air is introduced under pressure to keep the particulate matter of stack 10 from entering the passive reflector housing 26. A port 32 is provided for exhaust of the air.

Turning to FIG. 2, a light source 34 is provided in the transceiver 12 which projects a collimated light beam of uniform intensity onto a mirror 36 which reflects the light through a reducing lens 38 and through a focusing lens 40 to a beam splitter 42 which separates the beam into a reference beam 44 transmitted to a reference detector 46. The measurement beam 48 is projected through a glass slide or window 50. This beam is projected in a "double pass" across the stack to the mirror 52 of passive reflector 14 and back to a measurement detector 54. The reference beam is also reflected back from reference box 46 off of beam splitter 42 to measurement detector 54. This detector 54 registers variations in the light transmittance caused by the amount of particulate in the effluent. By ratioing the measurement signal to the reference signal, light source variations and common detector sensitivity are canceled out of the stack measurements. The output signals generated by detector 54 are amplified and transmitted to an instrument control (not shown), such as a Unicom 700, manufactured by Lear Siegler Measurement Controls Corporation of Englewood, Colo. The clear stack measurement provides the reference level against which subsequential opacity measurements are compared.

The calibration apparatus 56 is shown in FIG. 3 and more diagrammatically in FIG. 2. It includes a frame 58 with an opening 60 adjacent window 50 through which measurement beam 48 passes. The calibration apparatus 56 includes a zero reflector 62 and a span filter 64 whose construction and function can best be understood by reference to FIGS. 4–10. Zero reflector 62 includes a frame 66 with glass 68 mounted on one side, as shown in FIG. 10, the measurement beam 48 is projected through glass 68 and through an iris mechanism 70 onto a reflective surface 72 whereupon the projection beam is reflected back in the opposite direction. The frame 66 has a plate 76 formed integrally on one side thereof and is fixedly mounted on rotatable shaft 78 which is journalled in spaced brackets 80 and 82. The shaft is rotated by calibration motor 84 so that it can be moved from the position in FIG. 4 where it is out of the path of measurement beam 48 to a second position, as shown in FIG. 5, where it is directly in the path of measurement beam 48 so that the beam strikes the zero reflector and is reflected back. Conveniently, a limit switch 82 is closed by plate 76, when zero reflector 64 is pivoted to its inactive position, shown in FIG. 4, and a second limit switch 83 is closed by plate 76 when zero reflector is pivoted to its active position, shown in FIGS. 5 and 6 to shutoff calibration motor 84 at each limit of movement. Conveniently, as best seen in FIGS. 9 and 10, the iris mechanism 70 has a back plate 86 with a pair or arcuate slots 88 through which set screws 90 extend, respectively for locking the iris mechanism 70 in a fixed position. Prior to locking the iris in the fixed position, its position can be adjusted by rotation of set screws 94 and 96 which each bear against opposite sides of arm 98, as shown. By rotation of the iris, zero reflector 62 can be adjusted so that the light reflected by it will be identical to that reflected by passive reflector 14 when no particulate matter is passing through stack 10, i.e., the stack is clear. The proper alignment of back plate 86 on iris 70 is maintained by positioning pins 100 and 102, as shown. Thus, by positioning zero reflector 62 in the path of projection beam 48, the zero calibration for the equipment can be determined during initial set-up before operations begin. While the zero reflector 62 is in the path of measurement beam 48, span filter 64 can be rotated into a position in front of it. The span filter 64 includes a frame 104 attached to an arm 106 which is mounted for pivotal rotation with a shaft 108 within a solenoid 110 mounted on a bracket 112. Solenoid 110 is energized to rotate span filter 64 from its inoperative position to its operative position in front of measurement beam 48. Within frame 104 is a grid 114 having parallel spaced cross members 116, such as flat wires, which defuses some of the light to give an upper span range of the reflected light which will be above any practical range of light dispersion created by the particulate matter moving up stack 10. After these calibrations are made, both the span filter 64 and zero reflector 62 are moved back to their inoperative positions by calibration motor 84 and solenoid 110, respectively, and the apparatus is used to measure particulate matter as it flows through the stack.

As the device is used on a stack, even with the air purging apparatus previously described, the window 50 will become dirty causing a change in the readings obtained from reflected measurement beam 48. Therefore, on a periodic basis, the zero reflector will be swung back into the beam blocking position and a new zero reading will be obtained. Next, the span filter will be moved into a position in front of zero reflector 62 so that a new span reading can also be made. The electronics is then adjusted to reflect these new zero and span readings. The zero reflector and span filter are then swung out of the path of projection beam 48 and the apparatus continues to operate with the new settings. After a predetermined period has passed the resetting procedure will be repeated.

From the foregoing, the advantages of this invention are readily apparent. A single light source is used both for actual measurements and for zero and span settings so that any deterioration in the light source as it is used will be corrected each time a new zero and span reading is made. In addition, these new readings will account for any decrease in the passage of light through window 50 as it becomes dirty through use.

This invention has been described in detail with reference to a particular embodiment thereof, but it will be understood that various other modifications can be effected within the spirit and scope of this invention.

What is claimed is:

1. An improved apparatus for a full-system zero check and window soiling measurement and correction for a transmissometer, wherein the transmissometer includes a transceiver mounted on one side of a smoke stack and a retro-reflector is mounted on the opposite side of the stack, the transceiver having a primary light source, lens means for directing a beam of light from the light source through a window and across the smoke stack to the retro-reflector, the light beam being reflected back across the stack and through the window and lens means to the transceiver to measure the opacity level of smoke in the stack, said apparatus comprising:
a calibration device mounted between said transceiver and the one side of the stack and within the path of the light beam;
a zero reflector mounted within said calibration device for movement back and forth between an inactive position and an active position within the path of the light beam to reflect the same amount of light back into said transceiver as the retro-reflector would reflect across the stack when the stack is clear of smoke; and
means connected to said zero reflector for moving it from said inactive position to said active position and back again.

2. Apparatus, as claimed in claim 1, further including:
a filter mounted within said calibration device for movement from an inactive position to an active position within the path of the light beam and back again so that it is superimposed on said zero reflector to provide an upscale reference calibration check; and
means connected to said filter for moving it between said inactive position and said active position.

3. Apparatus, as claimed in claim 2, wherein:
said zero reflector moving means includes a motor.

4. Apparatus, as claimed in claim 3, further including:
a first limit switch positioned to be closed when said zero reflecting means is moved to its inoperative position to shut-off said motor in that position; and
a second limit switch positioned to be closed when said zero reflecting means is moved to its operative position to shut-off said motor in that position.

5. Apparatus, as claimed in claim 2, wherein:
said filter moving means includes a solenoid.

6. Apparatus, as claimed in claim 2, wherein:
said zero reflector and said filter are pivoted about different axes.

7. Apparatus, as claimed in claim 1, wherein said zero reflector includes:
an iris; and
means for adjusting said iris for initial zero calibration.

8. A method of calibrating the opacity readings of a transmissometer having a transceiver which is mounted on one side of a smoke stack and normally projects a light beam from a light source therein through a window and across the smoke stack where it is reflected back by a retro-reflector, mounted on the opposite side of the stack, to the transceiver which measures the amount of light detected, said method comprising.
projecting a light beam from the light source toward the retro-reflector across the stack;
moving a zero reflector into the light beam on the one side of the smoke stack, the zero reflector reflecting back to the transceiver the same amount of light as the retro-reflector would across the stack when it is clear of smoke;
recording and storing a zero value indicative of a clear smoke stack;
moving a filter into the light beam adjacent the zero reflector to cause the reflected light sensed by the transceiver to provide an upper span reading; and
recording and storing the upper span reading.

9. A method, as claimed in claim 8, including the further steps of:
moving the zero reflector and the filter to an inactive position out of the light beam path so that the light beam is projected across the stack and reflected back by the retro-reflector to the transceiver;
recording the amount of light sensed by the transceiver over an predefined period of time;
comparing the amount of light sensed by the transceiver over the predefined period of time with the previously recorded zero value and upper span reading to determine the opacity of smoke passing through the stack during the predefined period of time.

10. A method, as claimed in claim 9, including the further steps of:
moving the zero reflector back into the light path at the end of the predetermined period of time;
recording a zero offset value indicative of dirt accumulation on the window during the predetermined period of time;
moving the filter back into the light path;
recording a new upper span reading; and
repeating the steps of claim 9.

* * * * *